United States Patent [19]

de la Fuente

[11] Patent Number: 5,269,457
[45] Date of Patent: Dec. 14, 1993

[54] MEDICAL WASTE CONTAINER

[75] Inventor: Carlos de la Fuente, Corona, Calif.

[73] Assignee: Container Corporation of America, Clayton, Mo.

[21] Appl. No.: 19,710

[22] Filed: Feb. 19, 1993

[51] Int. Cl.5 .................... B65D 5/24; B65D 43/14
[52] U.S. Cl. ...................... 229/143; 206/366; 229/145; 229/149; 229/151; 229/186; 229/907
[58] Field of Search ........... 229/142, 143, 145, 147, 229/149, 151, 152, 186, 907; 220/908; 206/366

[56] References Cited

U.S. PATENT DOCUMENTS

| 1,184,689 | 5/1916 | Houghland | 229/142 |
|---|---|---|---|
| 1,749,675 | 3/1930 | Rouis | 229/143 |
| 2,330,466 | 9/1943 | Bergstein | 229/145 |
| 2,428,845 | 10/1947 | Guyer | 229/186 |
| 2,443,431 | 6/1948 | Ringler | 229/142 |
| 2,549,048 | 4/1951 | Bergstein | 229/145 |
| 3,441,193 | 4/1969 | Castle | 229/142 |
| 4,315,592 | 2/1982 | Smith | 229/149 |
| 4,674,676 | 6/1987 | Sandel et al. | 229/149 |
| 4,863,052 | 9/1989 | Lambert | 229/907 |
| 5,096,114 | 3/1992 | Higginbotham | 229/907 |

FOREIGN PATENT DOCUMENTS 274645 7/1951 Switzerland ............ 229/143

Primary Examiner—Gary E. Elkins
Attorney, Agent, or Firm—Richard W. Carpenter

[57] ABSTRACT

A collapsible, paperboard waste container that is particularly suitable to use for the receipt and retention of waste material such as medical waste. The container has a pair of integral, nesting, inner and outer covers with aligned covered openings that serve to prevent waste material from coming out of the container accidentally.

16 Claims, 4 Drawing Sheets

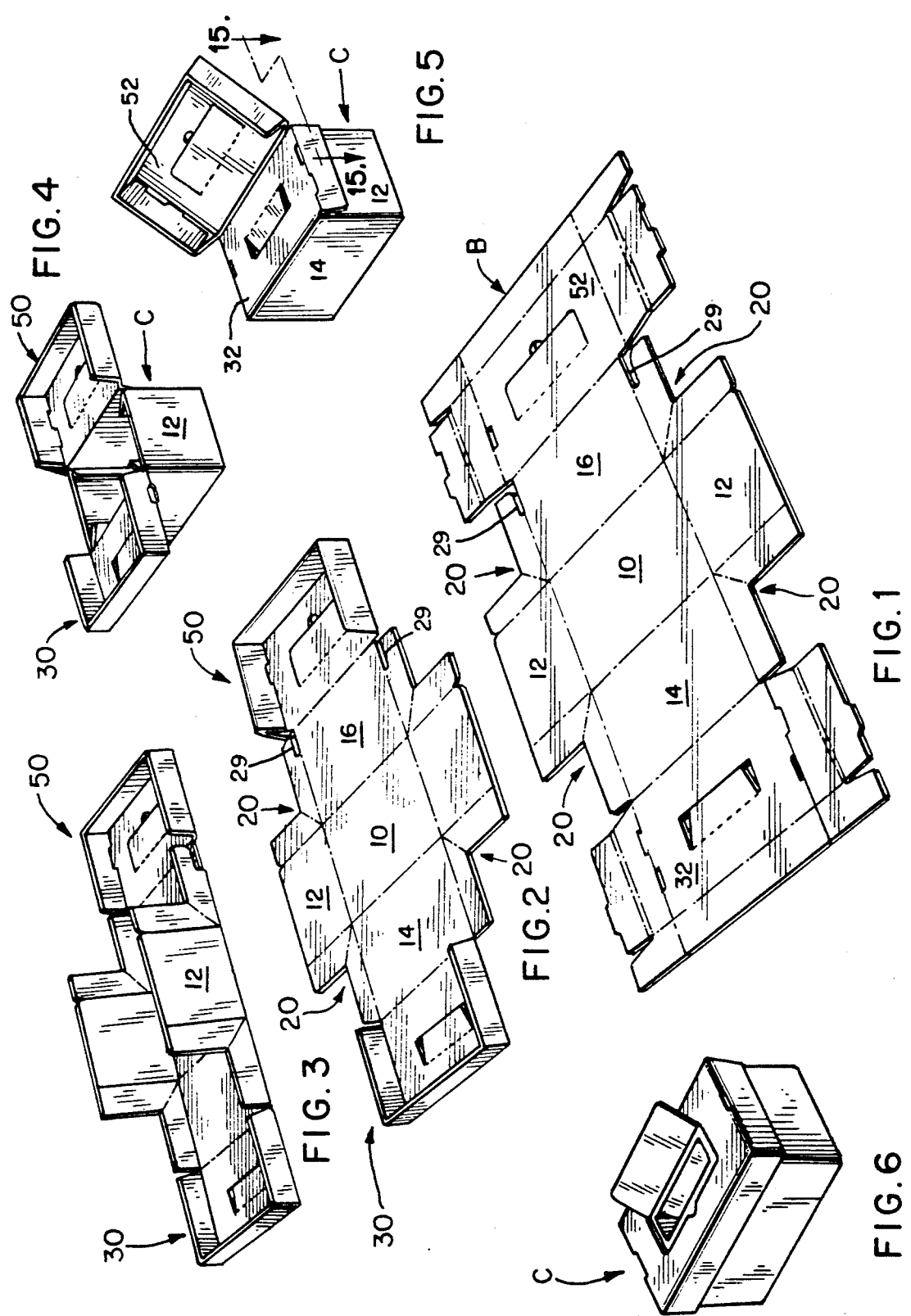

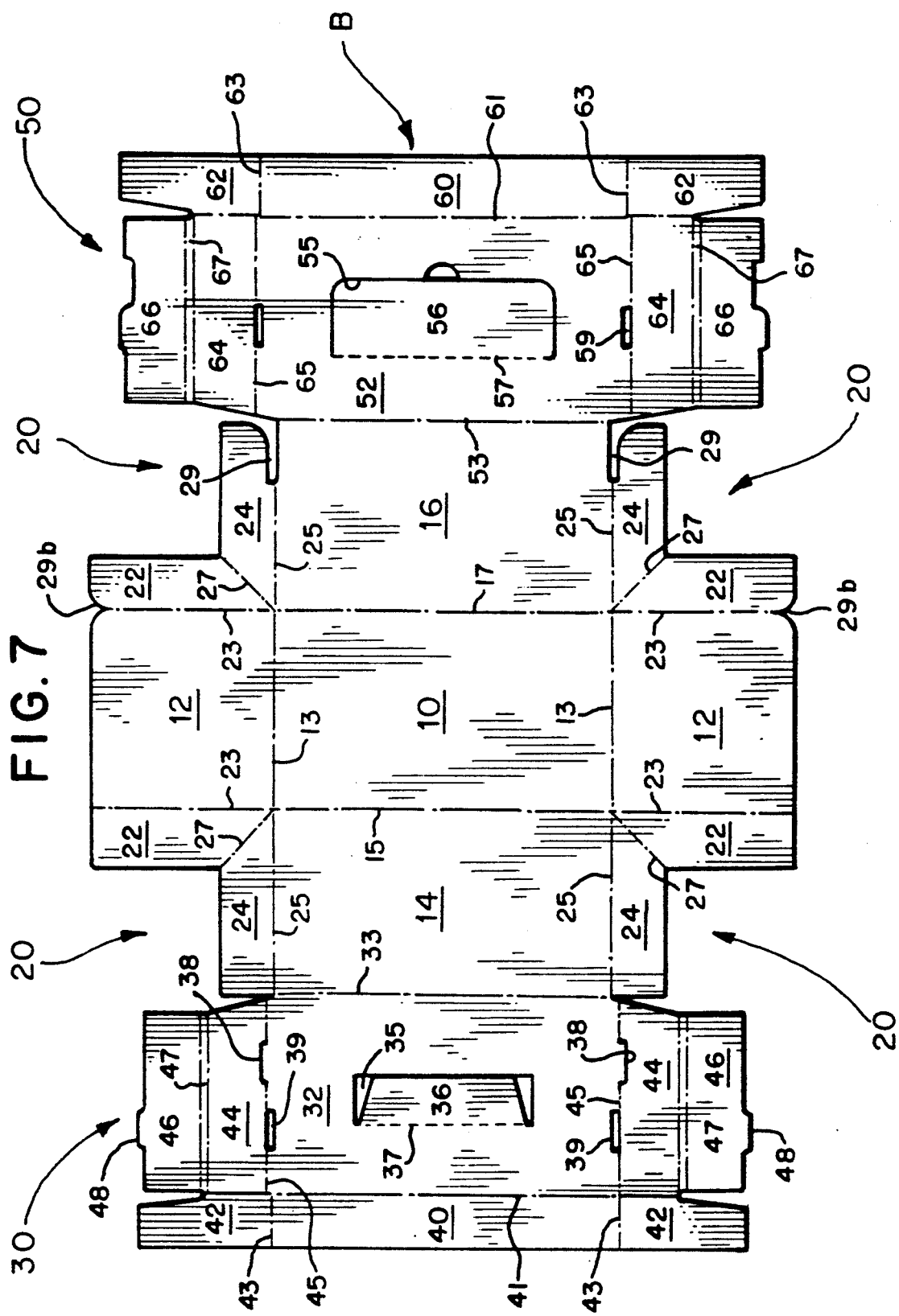

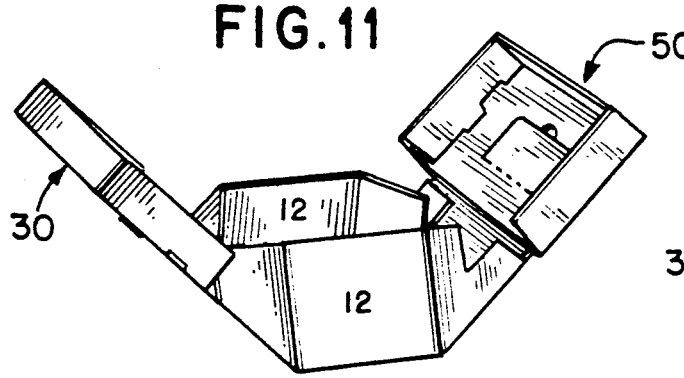
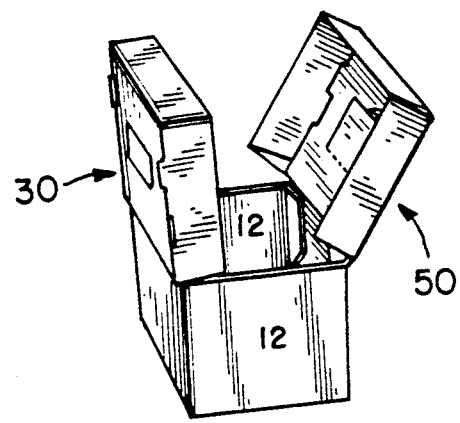
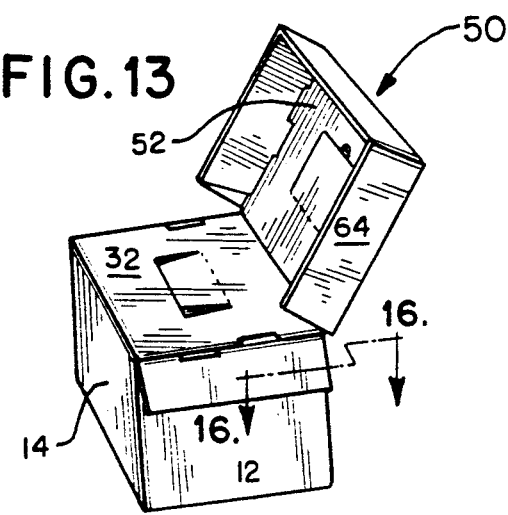
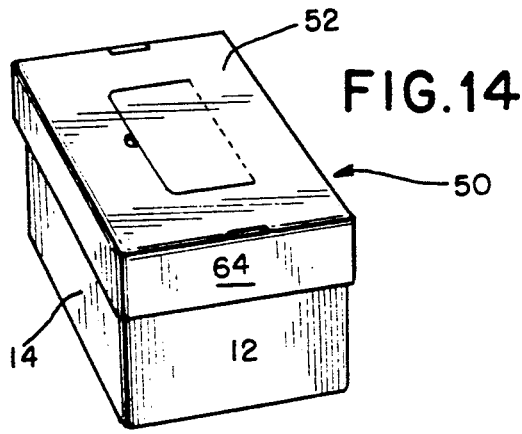
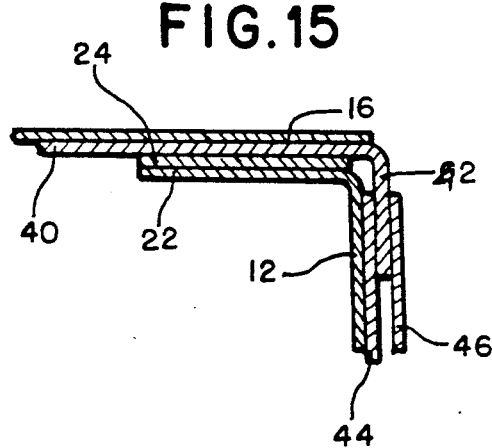
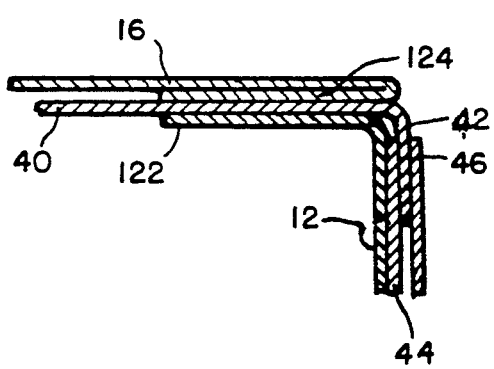

MEDICAL WASTE CONTAINER

BACKGROUND OF THE INVENTION

Field of the Invention

This invention relates to collapsable containers, and more particularly to paperboard containers that are especially suitable for receiving and holding contaminated waste material such as medical and/or hospital waste material.

SUMMARY OF THE INVENTION

It is a primary object of the invention to provide a waste container that is particularly suitable and convenient to use for the receipt and retention of waste material such as medical waste.

Another object of the invention is the provision of a waste container that is collapsible and is formed from a unitary blank of foldable sheet material, such as corrugated paperboard.

Still another object of the invention is to provide a container of the type described that has a cover closure arrangement that facilitates the insertion of waste material into the container, and, at the same time, prevents material from coming out of the container.

A more specific object of the invention is to provide a container of the type described that has a pair of integral, nesting, inner and outer covers with aligned covered openings.

These and other objects of the invention will be apparent from an examination of the following description and drawings.

BRIEF DESCRIPTION OF THE DRAWINGS

FIG. 1 is a perspective view of a blank of foldable sheet material from which the container embodying feature of the present invention and illustrated in FIGS. 4-6 and 15 can be formed;

FIGS. 2 and 3 are views similar to that of FIG. 1, but illustrate various steps in the formation of the container from the blank;

FIGS. 4-6 are additional perspective views illustrating a method of erecting and closing the container;

FIG. 7 is an enlarged plan view of the structure illustrated in FIG. 1;

FIGS. 9-14 are perspective views similar to those of FIGS. 1-6, but illustrate a method of erecting and closing the container formed from the blank of FIG. 8; and FIGS. 15 and 16 are fragmentary, horizontal, sectional views taken on lines 15—15 and 16—16 of FIGS. 5 and 13, respectively.

Figure 8:
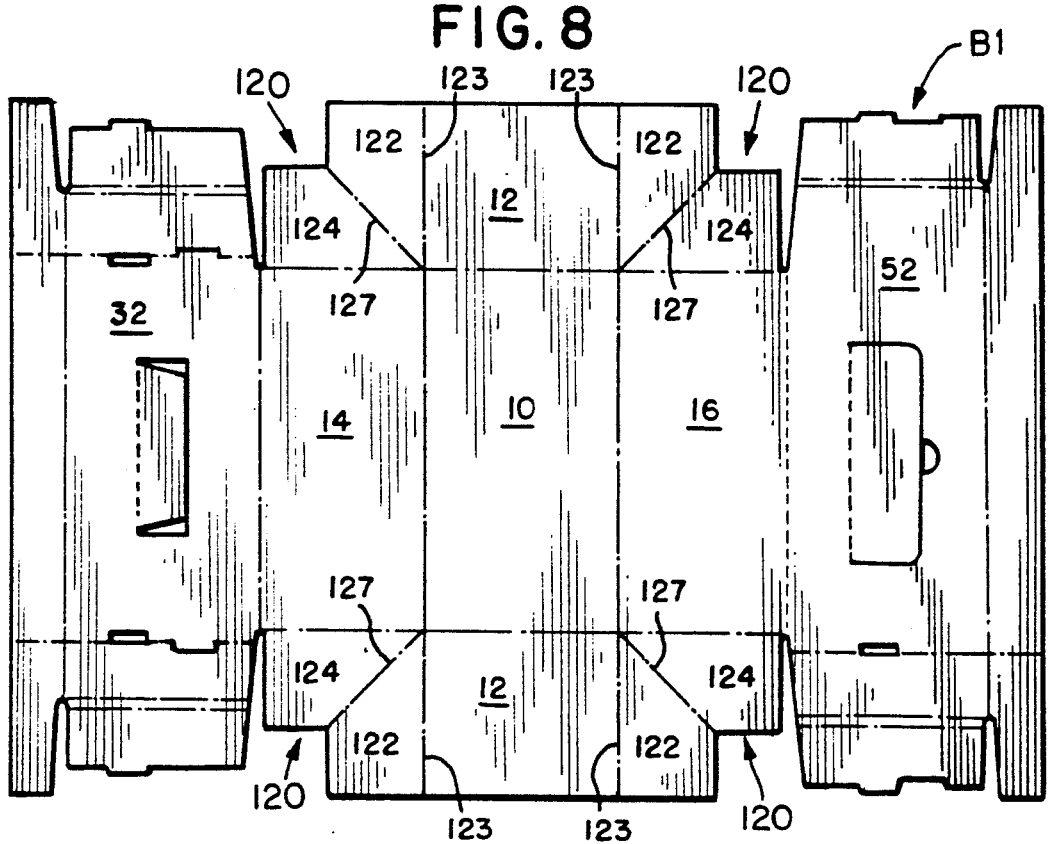
FIG. 8 is a view similar to that of FIG. 7, but illustrating a slightly modified form of the invention.

It will be under stood that, for purposes of clarity, certain elements may have been omitted from certain views where they are believed to be illustrated to better advantage in other views.

DESCRIPTION OF THE PREFERRED EMBODIMENT

Referring now to the drawings for a better understanding of the invention, It will be seen that the container embodying features of the invention, and indicated generally at C in FIG. 5, can be formed from the unitary blank B of, preferably plastic coated, corrugated, paperboard illustrated in FIG. 7 of the drawings.

Container C includes a body, indicated generally at 8, and a pair of integral, inner and outer covers 30 and 50, respectively.

As best seen in FIGS. 1 and 7, body 8 includes a preferably rectangular bottom wall panel 10 having a pair of end wall panels 12 foldably joined to opposed end edges thereof along fold lines 13, and having a pair of front and rear side wall panels 14 and 16 foldably joined to front and rear side edges thereof along fold lines 15 and 17, respectively.

At each corner of the container adjacent body side walls are foldably joined to each other by a web or gusset member, indicated generally at 20. Each gusset member 20 includes an end flange 22, foldably joined to a side edge of a body end wall panel along a fold line 23, and a side flange 24, foldably joined to an end edge of a body side wall panel along a fold 25.

The end and side flanges of each gusset member are foldably joined to each other along a diagonal fold line 27 extending outwardly from a related corner of the body bottom wall panel 10.

As best seen in FIG. 7, the side flanges connected to the front side wall panel 16 are each provided with a notch or slot 29 extending downwardly a relatively short distance from the upper edge thereof. The purpose of these slots is to receive portions of an inner cover flange, as described later herein.

As previously mentioned a pair of inner and outer covers 30 and 50 are foldably joined to the body front and rear side wall panels, respectively. Inner cover 30 includes includes a top wall panel 32 foldably joined to an upper edge of body front side wall panel 14 on a fold line 33.

Top wall panel 32 is provided with a preferably centrally disposed opening 35 to accomodate insertion of material into the container. Opening 35 is normally covered by a closure flap 36 which is formed from material of the top wall panel and has a side edge foldably joined thereto along a fold line 37.

Projecting outwardly from each end edge of top wall panel 32 is a lock tab 38. Also, located inwardly adjacent each end edge of panel 32, and spaced a short distance from related tab 38, is an opening 39 extending through panel 32. The purpose of the tabs 38 and openings 39 are described later herein.

A rear flange 40 is foldably joined, along fold line 41, to the rear side edge of top wall panel 32. Flange 40 has a a pair of corner flaps 42 foldably joined to opposed end edges thereof on fold lines 43.

At each end of panel 32 is an end flange which includes an outer panel 44, foldably joined on fold line 45 to the related end edge of panel 32, and an inner panel 46, foldably joined on fold line 47 to the lower edge of related outer panel 44. Each panel 46 has, projecting upwardly from its lower edge, a lock tab 48 adapted to be received within a related opening 39 in top wall panel 32, when the inner cover 30 is erected as described later herein.

Outer cover 50 includes a top wall panel 52, foldably joined to an upper edge of body rear side wall panel 16 on a fold line 53 and which is also provided with a centrally disposed opening 55 to accomodate insertion of material into the container.

Opening 55, which is aligned with inner cover opening 35 when the container covers are closed, is also normally covered by a closure flap 56, formed from material of the top wall panel and having a side edge foldably joined thereto along a fold line 57.

Projecting outwardly from each end edge of top wall panel 52 is a lock tab 58. Also, located inwardly adjacent each end edge of panel 52, and spaced a short distance from related tab 58, is an opening 59 extending through panel 52. The purpose of the tabs 58 and openings 59 are described later herein.

A front flange 60 is foldably joined, along fold line 61, to the front side edge of top wall panel 52. Flange 60 has a pair of corner flaps 62 foldably joined to opposed end edges thereof on fold lines 63.

At each end of panel 52 is an end flange which includes an outer panel 64, foldably joined on fold line 65 to the related end edge of panel 52, and an inner panel 66, foldably joined on fold line 67 to the lower edge of related outer panel 64. Each panel 66 has, projecting upwardly from its lower edge, a lock tab 68 adapted to be received within a related opening 59 in top wall panel 52 when the outer cover 50 is erected, as described later herein.

FIGS. 1-5 illustrate the manner in which the container C is formed from the flat blank B of foldable paperboard. The first step is the erection of the inner and outer covers, which are each formed in the same way.

Both end flange panels at each end of a cover top wall panel and the related side flange are folded upwardly 90 degrees from the top wall panel at the same time. Then the corner flaps are folded 90 degrees inwardly against inner surfaces of related end flange outer panels. Both end flange inner panels are then folded 180 degrees toward the top wall panel to sandwich the related corner flaps between each pair of end flange inner and outer panels, with the inner panel lock tabs being inserted into the realted openings at the ends of the top wall panels to lock the panels together.

After both covers have been formed, the body end wall panels are folded upwardly 90 degrees from the bottom wall panel to the position illustrated in FIG. 3. At the same time the corner flanges of each of the gusset members are folded inwardly, so the gusset member side flanges lie against the upper surface of their related body side wall panels, with the end flanges extending inwardly about 90 degrees over their related body side wall panels.

At this time the body side wall panels are folded upwardly 90 degrees from the body bottom wall panel. As the side wall panels are folded upwardly, the gusset member flanges at each corner of the body are brought together until they are disposed in face-to-face relation with each other against the adjacent inner surfaces of the related side wall panels.

With the container body so erected, the inner cover can then be folded downwardly 90 degrees over the upper edges of the body rear side wall and end walls. Portions of the inner cover front flange are inserted into the related slots 29 in the rear gusset member side flanges to lock the body in erected and closed condition, as best seen in FIG. 15.

The outer cover can then be folded inwardly 90 degrees to nest over and completely enclose the inner cover. Thus, the container is ready for service. Material can be inserted into the container through the aligned inner and outer cover openings, and the opening cover flaps prevent material from coming out of the container accidentally.

FIGS. 8-14 and 16 illustrate a slightly modified form of the invention. As the structure of this embodiment is generally similar to that of the previously described embodiment, the same numerals have been used to describe comparable components of the structure.

The sole difference between the embodiments of the invention resides in the gusset member arrangement. In the embodiment illustrated in FIGS. 8-14 and 16, gusset members 120 each include an end flange 122, foldably joined to a side edge of a body end wall panel along a fold line 123, and a side flange 124, foldably joined to an end edge of a body side wall panel along a fold 125.

The end and side flanges of each gusset member are foldably joined to each other along a diagonal fold line 127 extending outwardly from a related corner of the body bottom wall panel 10.

In this embodiment, none of the gusset member side flanges 124 have any slots or openings for receiving portions of the inner cover. The cover locking is provided in a different way, as hereinafter described.

Figure 9:
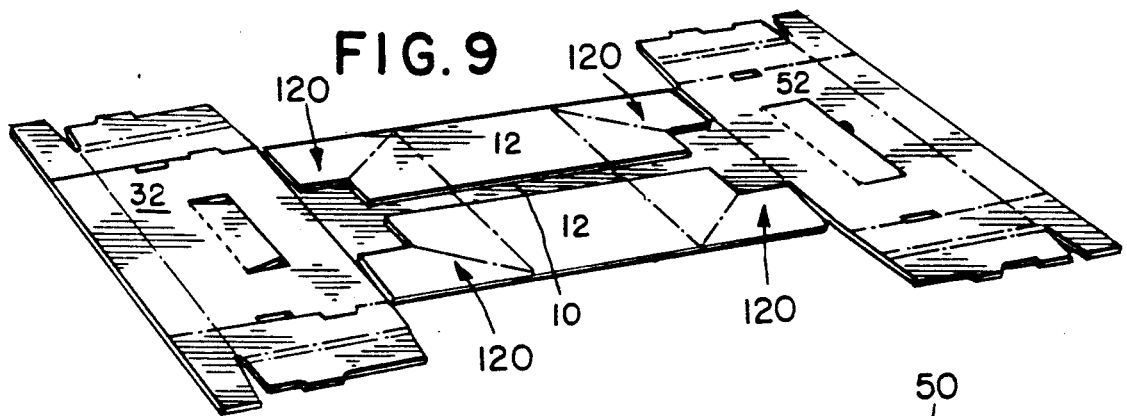
Figure 10:
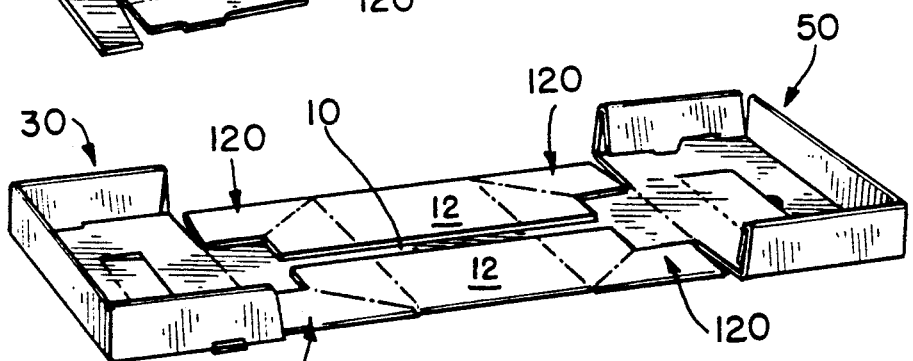

When the blank B1 of the container C1 is formed by the manufacturer, each of the body end wall panels and related gusset members are folded inwardly 180 degrees, so the end wall panels overlie the body bottom wall panel, and the gusset members overlie the adjacent body side wall panels. At this time the gusset member side flanges are adhesively secured to marginal portions of inner surfaces of their related body side wall panels, as illustrated in FIG. 9.

As illustrated in FIGS. 9-14, the container C1 is erected from the blank B1 in substantially the same manner as the container of the previously described embodiment.

The first step is the erection of the inner and outer covers, and they are erected in exactly the same way as the covers of the previous embodiment.

After the covers have been formed, the body side wall panels are folded upwardly 90 degrees from the body bottom wall panel. As the side wall panels move upwardly, the gusset member flanges at each corner of the body are brought together until they are disposed in face-to-face relation with each other against the adjacent inner surfaces of the related side wall panels.

With the container body so erected, the inner cover can then be folded downwardly 90 degrees over the upper edges of the body rear side wall and end walls. Portions of the inner cover front flange are inserted into between the rear surfaces of the rear gusset side flanges and the front surface of the body rear side wall to lock the body in erected and closed condition, as best seen in FIG. 16.

The outer cover can then be folded inwardly 90 degrees to nest over and completely enclose the inner cover. Thus, the container is ready for service. Material can be inserted into the container through the aligned inner and outer cover openings, and the opening cover flaps prevent material from coming out of the container accidentally.

What is claimed is:

1. A collapsible sanitary container for receiving and holding contaminated waste material, said container being formed from a unitary blank of foldable paperboard, and comprising:
   (a) a container body including a bottom wall panel having a pair of front and rear side wall panels foldably joined to and upstanding from front and rear side edges thereof and a pair of end wall panels foldably joined to and upstanding from opposed end edges thereof;

(b) said side and end wall panels being joined to each other at each corner of said container body by a gusset member;

(c) a pair of overlapping, interengaging, integral, inner and outer container covers each including a top wall panel having a pair of front and rear side edges, a pair of end edges, a side flange joined to and depending from one of said side edges, and a pair of end flanges joined to and depending from said end edges;

(d) said inner cover having its front side edge foldably joined to an upper edge of said body front side wall panel, and said outer cover having its rear side edge foldably joined to an upper edge of said body rear side wall panel;

(e) said inner and outer cover top wall panels having centrally disposed, aligned openings and closure flaps hinged to said top wall panels at corresponding edges of said openings;

(f) said inner cover top wall panel being slightly smaller than said outer cover top wall panel, so that, when the covers are folded over into overlapping relation to close the container, the inner cover will completely nest within the outer cover, with said inner cover side flange interposed between said container body rear side wall panel and adjacent side edges of said container body end wall panels.

2. A container according to claim 1, wherein said gusset member includes a pair of side sections adhesively secured to a related of said body side wall panels in face-to-face relation.

3. A container according to claim 1, wherein said gusset member includes a pair of side sections free from adhesive attachment to a related of said of body side wall panels.

4. A container according to claim 2, wherein said inner cover side flange is positioned between adjacent gusset member side and end sections to hold said container body panels in position when said container is erected.

5. A container according to claim 3, wherein said inner cover side flange is positioned adjacent a related of said body side wall panels and related of said gusset member side sections with portions of said cover side flange being received within slots in said gusset members to hold said container body panels in position when said container is erected and closed.

6. A container according to claim 1, wherein each of said cover end flanges includes a pair of inner and outer panels positioned adjacent each other in parallel relation.

7. A container according to claim 1, wherein each of said cover side flanges comprises a single panel having foldably joined to opposite ends thereof a pair of corner flaps each of which is interposed between related inner and outer panels of adjacent of said cover end flanges.

8. A collapsible sanitary container for receiving and holding contaminated waste material, said container being formed from a unitary blank of foldable paperboard, and comprising:

(a) a container body including a bottom wall panel having a pair of front and rear side wall panels and a pair of end wall panels foldably joined to and upstanding from front and rear side edges and opposed end edges thereof, respectively;

(b) said side and end wall panels being joined to each other at each corner of said container body by a gusset member;

(c) a pair of overlapping, interengaging, integral, inner and outer container covers each including a top wall panel having a pair of front and rear side edges, a pair of end edges, a side flange joined to and depending from one of said side edges, and a pair of end flanges joined to and depending from said end edges;

(d) said inner cover having its front side edge foldably joined to an upper edge of said body front side wall panel, and said outer cover having its rear side edge foldably joined to an upper edge of said body rear side wall panel;

(e) said inner and outer cover top wall panels having centrally disposed, aligned openings and closure flaps hinged to said top wall panels at corresponding edges of said top wall panel respective openings;

(f) said inner cover top wall panel being smaller than said outer cover top wall panel, so that, when said covers are folded into overlapping relation, the inner cover will nest within the outer cover, with said inner cover side flange interposed between said body rear side wall panel and adjacent side edges of said body end wall panels.

9. A container according to claim 8, wherein each of said gusset members includes a pair of side and end sections foldably joined to adjacent end and side edges of related of said side and end wall panels, respectively, and foldably joined to each other along a diagonal fold line extending outwardly from a related of said corners of said bottom wall panel.

10. A container according to claim 9, wherein said gusset member includes a pair of side sections each adhesively secured to a related of said body side wall panels in face-to-face relation.

11. A container according to claim 9, wherein said gusset member includes a pair of side sections free from adhesive attachment to a related of said body side wall panels.

12. A container according to claim 10, wherein said inner cover side flange is positioned between adjacent gusset member side and end sections to hold said container body panels in position when said container is erected.

13. A container according to claim 11, wherein said inner cover side flange is positioned adjacent a related of said body side wall panels and related of said gusset member side sections with portions of said cover side flange being received within slots in said gusset members to hold said container body panels in position when said container is erected and closed.

14. A container according to claim 8, wherein each of said cover end flanges includes a pair of inner and outer panels positioned ajacent each other in parallel relation.

15. A container according to claim 8, wherein each of said cover side flanges comprises a single panel having foldably joined to opposite ends thereof a pair of corner flaps each of which is interposed between related inner and outer panels of adjacent of said cover end flanges.

16. A unitary blank of foldable sheet material for use in forming a collapsible sanitary container for receiving and holding contaminated waste material, said blank being cut and scored to provide:

(a) a container body including a generally rectangular container body bottom wall panel having a pair of front and rear side wall panels foldably joined to front and rear side edges thereof and a pair of end wall panels foldably joined to opposed end edges thereof;

(b) said side and end wall panels being joined to each other adjacent each corner of said bottom wall panel by a gusset member;

(c) each of said gusset members including a pair of side and end sections foldably joined to adjacent end and side edges of related of said side and end wall panels, respectively, and foldably joined to each other along a diagonal fold line extending outwardly from a related one of said corners of said bottom wall panel;

(d) a pair of container inner and outer cover top wall panels each having one side edge foldably joined to a side edge of an adjacent one of said container side wall panels and having a second side edge and a pair of end edges;

(e) each of said cover top wall panels having foldably joined to its said second side edge a side flange panel and having foldably joined to its said end edges a pair of end flange panels;

(f) said inner and outer cover top wall panels having centrally disposed openings and closure flaps hinged to said top wall panels at corresponding edges of said top wall panel respective openings;

(g) said inner cover top wall panel being slightly smaller than said outer cover top wall panel, so that, when the container body and covers are erected and said covers are folded over into overlapping relation to close the container, said inner cover will completely nest within said outer cover.

* * * * *